United States Patent
Le Peltier et al.

(10) Patent No.: US 6,600,082 B2
(45) Date of Patent: Jul. 29, 2003

(54) PROCESS FOR DEHYDROGENATING ORGANIC COMPOUNDS IN THE PRESENCE OF A SUPPORTED BIMETALLIC CATALYST WITH A STRONG INTERACTION BETWEEN A GROUP VIII METAL AND TIN

(75) Inventors: Fabienne Le Peltier, Rueil-Malmaison (FR); Blaise Didillon, Francheville (FR); Jean-Claude Jumas, Jacou (FR); Josette Olivier-Fourcade, Jacou (FR)

(73) Assignee: Institut Francais du Petrole, Rueii-Malmaison (FR)

( * ) Notice: Subject to any disclaimer, the term of this patent is extended or adjusted under 35 U.S.C. 154(b) by 21 days.

(21) Appl. No.: 09/934,598

(22) Filed: Aug. 23, 2001

(65) Prior Publication Data

US 2002/0045787 A1 Apr. 18, 2002

(30) Foreign Application Priority Data

Aug. 23, 2000 (FR) .............................. 00 10879

(51) Int. Cl.$^7$ ........................... C07C 5/41; C07C 5/367; C07C 5/333
(52) U.S. Cl. ...................... 585/434; 585/380; 585/444; 585/445; 585/623; 585/629; 585/631; 585/661; 585/662; 585/663
(58) Field of Search ................ 585/434, 380, 585/444, 445, 623, 624, 631, 661, 662, 663

(56) References Cited

U.S. PATENT DOCUMENTS

| | | | | |
|---|---|---|---|---|
| 3,531,543 A | | 9/1970 | Clippinger et al. | 260/683.3 |
| 3,691,102 A | | 9/1972 | Swift | 252/469 |
| 4,716,143 A | | 12/1987 | Imai | 502/326 |
| 5,128,300 A | * | 7/1992 | Chao et al. | 502/227 |

FOREIGN PATENT DOCUMENTS

EP  0 248 130 A1  12/1987

OTHER PUBLICATIONS

XP–002158598—A Mössbauer Spectroscopy Study of Platinum–Tin Reforming Catalysts, M.C. Hobson, Jr., et al., Journal of Catalysis 142, pp. 641–654 (1993).

* cited by examiner

Primary Examiner—Thuan D. Dang
(74) Attorney, Agent, or Firm—Millen White Zelano & Branigan

(57) ABSTRACT

A process for dehydrogenating organic compounds, in particular paraffins and naphthenes, is carried out in the presence of a supported catalyst comprising a group VIII metal such as platinum, and tin, at least a portion of which interacts strongly with the group VIII metal in the catalyst in the reduced state. In the partially oxidised state, the catalyst contains at least 10% of tin in the form of a reduced tin species with oxidation state 0, said species having an isomer shift in the range 0.80 to 2.60 mm/s and a quadrupolar splitting in the range 0.65 to 2.00 mm/s.

29 Claims, No Drawings

PROCESS FOR DEHYDROGENATING ORGANIC COMPOUNDS IN THE PRESENCE OF A SUPPORTED BIMETALLIC CATALYST WITH A STRONG INTERACTION BETWEEN A GROUP VIII METAL AND TIN

FIELD OF THE INVENTION

The present invention relates to a process for dehydrogenating organic compounds, in particular paraffins and naphthenes, to produce alkenes and aromatic compounds with optimised yields. The process of the invention is carried out in the presence of a bimetallic supported catalyst comprising a group VIII metal and at least one additional metal constituted by tin, at least a portion of which interacts strongly with said group VIII metal.

Aromatic compounds and alkenes constitute the feeds of choice for the petrochemicals industry.

Processes for dehydrogenating light paraffins can upgrade aliphatic hydrocarbons with a low boiling point, such as butanes and isobutanes, pentanes and isopentanes, that can be recovered after extracting the unsaturated compounds from steam cracked or catalytically cracked cuts. The process for dehydrogenating longer paraffins is an important commercial process because of the current demand for monoolefins to prepare biodegradable detergents or pharmaceutical products, for example.

While the principal sources of alkenes are catalytic cracking and steam cracking processes, these two processes also produce by-products and with increasing demand being oriented towards specific alkenes, it would not make economic sense to produce them by cracking.

For this reason, the direct production of alkenes remains in some cases an unavoidable step. This is the case for propylene, isobutene and linear long chain alkenes for the production of polypropylene, MTBE and LAB (linear alkyl benzene) respectively.

The principal features of the paraffin dehydrogenation reaction are because thermodynamic equilibrium limits the degree of conversion per pass and that the reaction is highly endothermic. These two characteristics determine the technological choice regarding the process and also the composition, structure and design of the catalyst.

High temperature operations are necessary to maintain a level of conversion close to thermodynamic equilibrium, but such high temperatures also encourage a certain number of side reactions leading to a lower quality product. Such reactions include reactions resulting in the formation of light products (cracking, hydrogenolysis), of highly unsaturated compounds that are precursors for carbonaceous deposits and thus initiators of deactivation (dehydrocyclisation, deep dehydrogenation) such as aromatic compounds or diolefins and skeletal isomerisation reactions responsible for the formation of branched molecules. Under those particularly severe operating conditions, it is very difficult to maintain high activity for long periods because of those secondary reactions.

PRIOR ART

Means for limiting those secondary reactions can be based on the process and/or on the catalytic formulation. To improve the performance of catalytic systems, in particular their stability, U.S. Pat. No. 4,716,143 describes a catalyst based on supported platinum wherein the distribution of the platinum is limited to the external surface of the support over a maximum depth of 400 µm The advantage of such a choice resides in the fact that a distribution on the support periphery can limit side reactions and as a result, improve the performance of the catalyst. However, that type of distribution can only rarely produce homogeneous platinum/modifier atomic ratios on the particle scale (nanometer). Further, an overconcentration of active phase can cause diffusional limitations in the catalyst grain (extragranular diffusion) and thus reduce the overall reaction yield.

A vast number of patents and publications demonstrate that adding promoters to a base metal improves the performance of the catalyst. Such elements are added in different forms such as salts or organometallic compounds. In general, more active or more selective catalysts are obtained, which are sometimes more stable than the corresponding monometallic catalyst.

The formulation of catalysts used in hydrocarbon transformation processes, in particular catalysts for catalytic reforming and paraffin dehydrogenation, has been the subject of a large number of studies. Of the more frequently used promoters, tin can increase the selectivity and stability of the catalysts. Catalysts based on PtSn supported on alumina and used in paraffin dehydrogenation have, for example, been described in French patent FR-B-2 031 984 and U.S. Pat. No. 3,531,543.

In particular, catalysts based on PtSn contain different forms of tin. In the reduced state, those catalysts, supported on alumina, essentially contain species of tin in the oxidised state, namely species of divalent tin $Sn^{II}$ and tetravalent tin $Sn^{IV}$, and minor quantities of tin in the reduced state $Sn^0$ (M. C. Hobson et al., J. Catal., 142, 641–654 (1993), L. D. Sharma et al., Appl. Catal. A Genneral., 168, 251–259, (1998)). Those catalysts are generally prepared from a solution of tin chloride in an acidic medium (HCl, $NHO_3$) and a hexachloroplatinic acid solution. The role of the tin present on the catalyst surface in oxidation state +2 or, more preferably, +4, is to minimise isomerisation and cracking reactions that occur at acidic sites on the support, and to limit coke formation to improve the stability of the catalyst.

One technique that can examine the local electronic structure of the tin (oxidation state, environment, chemical bonding) is Mössbauer spectroscopy, which directly provides two fundamental parameters: the isomer shift, $\delta$ (IS) and the quadrupolar splitting $\Delta$ (QS). The isomer shift $\delta$ measures the energy position of the Mössbauer absorption, a function of the density of the nucleus s, directly characterises the oxidation state of the tin. The quadrupolar splitting, $\Delta$, which defines the form of the absorption, is a function of the distribution of the surrounding charges, and characterizes the degree of coordination and thus the type of chemical bond in which the tin is involved. Each species of tin is characterized by a sub-spectrum defined by the two parameters IS and QS. Mössbauer spectroscopy also provides access to the line width LW, by comparison with the natural width of the emission (0.64 mm/s): the line width LW provides information regarding the degree of order and the distribution of the sites occupied by the tin. The relative intensity of the absorption for each species is proportional to the number of tin atoms and to the Mössbauer Lamb factor f, which represents the probability of resonant absorption without recoil and without thermal broadening. The factor f is directly related to the rigidity of the lattice and its value is increased by a reduction in the temperature of measurement. It can be small at ambient temperature (0.06 for the metallic β phase of tin) and thus requires measurements to be carried out at low temperatures. The proportion of each species is estimated from their contribution to the total absorption, provided that the recoil-free resonant absorption fractions f are not too different.

Characterisations using Mössbauer spectroscopy of reduced catalysts based on PtSn supported on alumina or silica mention the existence of a species $Sn^0$ contained in a $Pt_xSn_y$ type phase (x and y from 1 to 4) in which the tin is in oxidation state 0 (IS of 1.4 to 1.8 mm/s with respect to $BaSnO_3$) in a form that is very close to bulk alloys characterized by a low or zero quadrupolar splitting (M. C. Hobson et al., J. Catal., 142, 641–654 (1993); Z. Huang et al., J. Catal., 159, 340–352 (1993); J. L. Margitfalvi et al., J. Catal., 190, 474–477 (2000); V. I. Kuznetov et al., J. Catal., 99, 159 (1986); R. Bacaud et al., J. Catal., 69, 399 (1981); R. Srinivasan et al., Catal. Today, 21, 83 (1994)). On alumina, the formation of metallic tin in the reduced state, favoured with larger metallic particle sizes of more than 2 nm, is responsible for the loss in performance of PtSn catalysts supported on alumina (Z. Huang et al., J. Catal., 159, 340–352, (1993), F. Yining et al., Stud. Surf. Sci. Catal., 68, 683–690, (1991)). A number of documents describe the use of catalysts containing a PtSn phase dispersed on alumina or tin that is essentially in a higher oxidation state than that of metallic tin (U.S. Pat. Nos. 3,846,283, 3,847,794). Under such conditions, the conventional preparation methods used cannot guarantee a close association between tin and platinum, an intimate association between those metals in the catalyst in the reduced state being generally desirable, however, to best exploit the bimetallic effect in processes for transforming organic compounds.

SUMMARY OF THE INVENTION

The invention concerns a process for dehydrogenating organic compounds carried out in the presence of a novel supported catalyst containing at least one metal from group VIII of the periodic table and at least tin at least a portion of which interacts strongly with said group VIII metal. The supported catalyst used in the process of the invention is characterized in that it contains metallic particles, of small size, less than 2 nm, and in that at least 10% of the tin species present in the catalyst in the partially re-oxidised state are in the form of a reduced tin species with oxidation state 0. Said reduced species is in a particular form, as demonstrated by $^{119}Sn$ Mössbuaer spectroscopy, and is characterized by a very high quadrupolar splitting value of more than 0.65 mm/s and an isomer shift IS in the range 0.8 to 2.6 mm/s with respect to $BaSnO_3$. This species is revealed by carrying out perfectly controlled oxidation on the reduced catalyst using pulses of oxygen. This particular species of tin is very closely associated with the group VIII metal and reveals a very strong interaction between the atoms of said group VIII metal and at least a fraction of the tin in the catalyst in the reduced state. As an example, in the case where the group VIII metal is platinum, a $Pt_xSn_y$ phase is formed in which the tin has set values for IS and QS. Preferably, the catalyst also contains an alkali or alkaline-earth metal.

IMPORTANCE OF THE INVENTION

The catalyst used in the process of the invention has substantially improved catalytic properties with respect to prior art catalysts, in particular as regards activity and stability. It has surprisingly been discovered that the presence of a large quantity of a reduced tin species with oxidation state 0 and closely associated with a group VIII metal in a bimetallic catalyst that is partially oxidised by oxidation carried out under perfectly controlled conditions using pulses of oxygen, reveals a strong interaction in the reduced state of the catalyst between the group VIII metal and at least a fraction of the tin, guaranteeing a beneficial bimetallic effect on the catalytic performances of the units for dehydrogenating organic compounds, in terms of activity and stability, better activity and better stability very substantially increasing the alkenes and aromatics yield, the target products of paraffin and naphthene dehydrogenation reactions.

DESCRIPTION

The process for dehydrogenating organic compounds of the invention comprises bringing a hydrocarbon feed into contact with a supported catalyst comprising at least one metal from group VIII of the periodic table and tin, at least a portion of which interacts strongly with the group VIII metal in the catalyst in the reduced state. In the remainder of the description, a distinction is made between the catalyst in the reduced state and the partially oxidised catalyst in that the quantity of tin reduced to oxidation state 0 and in intimate association with a group VIII metal is higher in the partially oxidised catalyst.

The invention concerns dehydrogenation of all types of organic compounds. More precisely, it concerns the dehydrogenation of short paraffins, i.e., saturated aliphatic organic compounds containing 2 to 5 carbon atoms, the dehydrogenation of long paraffins, i.e., saturated aliphatic organic compounds containing 6 to 22 carbon atoms, and the dehydrogenation of naphthenes, i.e., saturated cyclic organic compounds. Within the context of the invention, the naphthenes are preferably selected from the group formed by methylcyclohexane and cyclohexane.

The hydrocarbon feed brought into contact with the catalyst can comprise compounds other than those to be dehydrogenated; in particular, it can contain aromatic compounds.

The support for the catalyst used in the process of the invention comprises at least one refractory oxide that is generally selected from oxides of metals from groups IIA, IIIA, IIIB, IVA or IVB of the periodic table, such as oxides of magnesium, aluminium, silicon, niobium, titanium, zirconium and thorium, taken alone or as a mixture or mixed with oxides of other elements from the periodic table. For organic dehydrogenation reactions, the preferred support is alumina, with a specific surface area advantageously in the range 5 to 400 $m^2$ per gram, preferably in the range 50 to 350 $m^2/g$. The support for the catalyst of the invention can also be a zeolite or molecular sieve of type X, Y, mordenite, faujasite, ZSM-5, ZSM-4, ZSM-8, MFI, EUO, mazzite and mixtures of oxides of metals from groups IIA, IIIA, IIIB, IVA and IVB with the zeolitic material, in particular aluminium oxide-zeolite mixtures.

The group VIII metal is the catalytically active base metal of the catalyst used in the process of the invention. Preferably, it is a noble metal from the platinum family (Pt, Pd, Rh, Ir). More preferably, the noble metal is platinum. Advantageously, the catalyst contains a first noble metal (such as Pt) to which iridium is added. When dehydrogenating organic compounds, in particular paraffins, platinum and iridium are preferred. The percentage by weight is selected so as to be in the range 0.01% to 10%, preferably in the range 0.05% to 5%.

The tin acts as a promoter. The percentage by weight of tin in the catalyst in the reduced state, including all species (reduced and oxidised) with respect to the total catalyst weight, is in the range 0.01% to 2%, for example. Very advantageously, the catalyst used in the process of the invention contains at least 0.1% by weight of tin. In accordance with the invention, tin is present in the reduced catalyst essentially in the oxidised state ($Sn^{II}$ and $Sn^{IV}$). An essential feature of the process of the invention is the use of a catalyst with a high proportion of metallic tin $Sn^0$ with respect to the oxidised tin species, when the catalyst is in the partially oxidised state, i.e., when the reduced catalyst has undergone perfectly controlled oxidation using pulses of oxygen. This species of metallic tin $Sn^0$ is in the very particular form of an VIII metal-Sn alloy, in which said group VIII metal and tin are intimately associated and strongly interact with oxygen. This species has very high QS values in the range 0.65 to 2.00 mm/s and is revealed when the catalyst is partially oxidised. The catalyst that is brought into contact with the hydrocarbon feed is characterized in that in the partially oxidised state, at least 10% of the tin with respect to the tin introduced is in the form of a reduced species with an oxidation state of 0, i.e., this reduced species with oxidation state 0 represents at least 10% of the tin present in the catalytic mass. Advantageously, said reduced tin species with oxidation state 0 represents at least 12% of the tin present in the catalytic mass. Preferably, it represents at least 15%, more preferably at least 20% and still more preferably at least 25%. Highly preferably, it represents at least 30%.

In the partially oxidised state of the catalyst, said reduced tin species generally does not represent more than 90% of the catalytic mass. Preferably, it does not represent more than 70% and more preferably, it does not represent more than 60%.

The term "catalyst in the partially oxidised state" means a catalyst that has been oxidised in a perfectly controlled manner using pulses of oxygen. In accordance with the invention, perfectly controlled oxidation of the catalyst in the reduced state can reveal, by Mössbuaer spectroscopy, the presence of a large quantity of metallic tin in intimate association with the group VIII metal, in particular platinum, and oxygen, the presence of said reduced tin species resulting in the existence of a strong interaction between said group VIII metal, preferably platinum, and at least a fraction of the tin in the catalyst in the reduced state. The catalyst in its partially oxidised state contains $Sn^{2+}$ species and said tin species reduced to oxidation state 0 ($Sn^0$) is in the particular form of an VIII metal-Sn alloy, preferably in the particular form of a Pt—Sn alloy.

When the reduced catalyst is oxidised under non controlled conditions such as re-oxidation in air with a high partial pressure of oxygen, the amount of the metallic tin species $Sn^0$ in the form of VIII metal-Sn alloy, preferably in the form of a PtSn alloy, reduces very substantially to the advantage of the formation of $Sn^{4+}$ species. The catalyst is then strongly oxidised and essentially comprises $Sn^{4+}$ species. It no longer contains $Sn^{2+}$ species. This formation of $Sn^{4-}$ species perturbs the quantification of Sn species strongly interacting with the group VIII metal, preferably platinum, present from the reduced state, and thus the performance of the catalyst in its reduced state cannot be appreciated. In contrast, controlled oxidation by pulsing can selectively form said reduced tin species $Sn^0$ with the Mössbuaer characteristics described above, avoiding the formation of Sn4- species.

The catalyst can also optionally contain 0.1% to 3% by weight of at least one alkali metal or alkaline-earth metal. Paraffin dehydrogenation is most preferably carried out with a catalyst comprising such an element (alkali or alkaline-earth). In order to dehydrogenate short paraffins, potassium is preferably used, and in order to dehydrogenate long paraffins, lithium is preferably used.

The catalyst can also contain at least one group IIIA element. The group IIIA element is selected from indium, gallium and thallium, preferably indium, in an amount in the range 0.005% to 3% with respect to the total catalyst weight, more preferably in the range 0.1% to 1%. Most advantageously, the catalyst used for dehydrogenating long paraffins contains indium. The catalyst can also optionally contain, for example, at least one halogen or a halogenated compound in proportions of the order of 0.1 to 3% by weight of catalyst. It can also optionally contain at least one metalloid such as sulphur in proportions of the order of 0.01% to 2% by weight of catalyst. It can also contain at least one other chemical element, for example rhenium or niobium, in proportions of the order of 0.01% to 3% by weight of catalyst, said element being introduced into the catalyst using any method and in any form that is known to the skilled person.

The catalyst can be in the form of beads, extrudates, trilobes or any other routinely used form. The catalyst of the invention contains metallic particles with small sizes, i.e., less than 2 nm. These metallic particles contain the noble metal and tin, the tin being mainly in oxidation state 0 in proportions as described above.

Analyses that can examine the local electronic structure of the tin are carried out in a conventional Mössbuaer spectroscopy provided with a $Ba^{119m}SnO_3$ γ radiation source with a nominal activity of 10 mCi. The spectrometer operates in transmission mode with a velocity transducer with a constant acceleration functioning in triangular mode with respect to a 512-channel multichannel analyser, controlled by a microcomputer. The detector is a 0.1 mm thick NaI (T1) crystal scintillator. The scale is calibrated using a standard 6-line α-Fe spectrum obtained with a $^{57}Co(Rh)$ source. All of the isomer shifts IS are given with respect to a $BaSnO_3$ standard. ISO software is used to resolve the experimental spectra into Lorentzian profiles and into the different parameters, plus the mean squares (W. Künding, Nucl. Instrum. Method., 75, 336 (1969)).

For certain analyses carried out at low temperature, a cryostat with a variable flow and temperature (4 to 300 K) is advantageous. Such measurements are necessary to characterize values of f relating to a given species.

The analyses are carried out using powdered catalysts, already reduced, in a hydrogen flow, between 450° C. and 550° C. After cooling to ambient temperature in hydrogen and flushing with a neutral gas such as helium, the reduced catalyst undergoes the number of pulses of oxygen necessary to saturate it. Pulsed injections are continued until at least 10 peaks are obtained with a constant surface area (chromatographic analysis), then the catalyst is flushed with a neutral gasoline such as helium, the treatment cell is sealed directly without ingress of air. The quantity of catalyst necessary, including the amount of tin, is at least 2 g. This cell can be used at ambient temperature or at low temperatures. The catalyst tested using Mössbuaer spectroscopy is in the partially re-oxidised state.

The catalyst used in the process of the invention and analysed by Mössbuaer spectroscopy in the partially oxidised form, contains tin in the oxidised form (divalent or tetravalent tin) and in the reduced form. In accordance with the invention, the $Sn^{IV}$ species are characterized by an isomer shift IS in the range 0 to 0.25 mm/s and with a quadrupolar splitting QS in the range 0 to 0.80 mm/s. $Sn^{II}$ species are characterized by an IS in the range 2.70 to 3.40 mm/s and a QS in the range 1.60 to 2.60 mm/s. $Sn^0$ species are characterized by an IS in the range 0.80 to 2.60 mm/s and a QS in the range 0.65 to 2.00 mm/s.

In accordance with the invention, said reduced tin species in oxidation state 0 ($Sn^0$) is a particular form of the VIII metal-Sn alloy, preferably in the particular form of a Pt—Sn alloy, with values of IS in the range 0.80 to 2.60 mm/s, preferably in the range 0.80 to 1.50 mm/s, more preferably in the range 1.10 to 1.40 mm/s and with values of QS in the range 0.65 to 2.00 mm/s, preferably in the range 0.80 to 2.00 mm/s, more preferably in the range 0.90 to 1.90 mm/s and still more preferably in the range 0.95 to 1.50 mm/s. Advantageously, said reduced tin species in oxidation state 0 ($Sn^0$), in the particular form of a VIII metal-Sn alloy, and in particular in the form of a PtSn alloy, and with values of IS and QS as given above, is only present in the catalyst in the partially oxidised state.

The values for the Mössbuaer parameters obtained for the catalyst in the partially oxidised state are the results of the existence of a strong interaction between the tin and the group VIII metal, this interaction being revealed by perfectly controlled oxidation of the reduced catalyst.

The very close association of these two metals in the catalyst of the invention can exploit to the limit the intrinsic properties of each metal and thus generates a synergistic effect that is even greater when the reduced tin species with oxidation state 0 is in a large quantity and has a high QS. As an example, when the group VIII metal is platinum, the reduced tin species is contained in a particular phase of the type $Pt_xSn_y$, where said reduced tin species and the platinum are in intimate association.

The tin precursor can be selected from the group formed by halogenated compounds, hydroxides, oxides, carbonates, carboxylates, nitrates and sulphates of tin, this list being non-limiting. It can be introduced in the form of at least one organic compound selected from the group formed by tin complexes, and hydrocarbyl tin compounds such as tin alkyls, cycloalkyls, aryls, alkylaryls and arylalkyls. The tin precursor can also be selected from the group formed by halogenated compounds, hydroxides, oxides, carbonates, carboxylates, nitrates and sulphates of organometallic tin compounds, this list being non-limiting. These compounds comprise at least one carbon-Sn bond. As an example, the tin precursor can be selected from polyalkyl halides, for example trimethyl halides ($Me_3SnX$), triethyl halides ($Et_3SnX$), dimethyl dihalides ($Me_2SnX_2$), diethyl dihalides ($Et_2SnX_2$), diisopropyl dihalides ($iPr_2SnX_2$), di-n-propyl dihalides ($n-Pr_2SnX_2$), methyl trihalides ($MeSnX_3$), ethyl trihalides ($EtSnX_3$), isopropyl trihalides ($i-PrSnX_3$), di-n-propyl trihalides ($n-PrSnX_3$), polyalkyl hydroxides, for example trimethyl hydroxides ($Me_3SnOH$), triethyl hydroxides ($Et_3SnOH$), dimethyl dihydroxides ($Me_2Sn(OH)_2$), diethyl dihydroxides ($Et_2Sn(OH)_2$), diisopropyl dihydroxides ($iPr_2Sn(OH)_2$), n-propyl dihydroxides ($n-Pr_2Sn(OH)_2$), methyl trihydroxides ($MeSn(OH)_3$), ethyl trihydroxides ($EtSn(OH)_3$), diisopropyl trihydroxides ($iPrSn(OH)_3$), n-propyl trihydroxides ($n-PrSn(OH)_3$), polyalkyl acetates, for example trimethyl acetate ($Me_3SnOC(O)Me$), triethyl acetate ($Et_3SnOC(O)Me$), tributyl acetate ($Bu_3SnOC(O)Me$), polyalkyl oxides, for example bis-trimethyl oxide ($[Me_3Sn]_2O$), bis-triethyl oxide ($[Et_3Sn]_2O$), bis-tripropyl oxide ($[Pr_3Sn]_2O$) bis-tributyl oxide ($[Bu_3Sn]_2O$), polyalkyl sulphates, for example bis-trimethyl sulphate ($[Me_3Sn]_2SO_4$), bis-dimethyl sulphate ($[Me_2Sn]_2SO_4$), methyl trioxo sulphate ($MeSnO_3$), where X represents a halogen selected from the group formed by fluorine, chlorine, bromine and iodine. The tin precursor can be selected from compounds with general formula $(R1)_xM(R2)_y(R3)_z$, where x+y+z=the valency of tin and where R1 is selected from the group formed by alkyl, cycloalkyl, nitrile (CN), carbonyl (CO), aryl, alkylaryl and arylalkyl radicals, where R2 is a function with the form $C_aH_bR'_c$, where R' represents a hydroxide, halide, carboxylate, $PO_3H$ or $SO_3H$ function and where R3 is an aquo, oxo (MO), alkoxide (O-alkyl), hydride, hydroxyl, alkylsulphonate, alkylsulphate, thioalkyl, $N(SO_3R")_2$, $PR"_2$ and $PR"_3$ group, where R" is an alkyl group ("Handbook of physics and chemistry", $63^{rd}$ edition, 1982–83).

The terms "alkyl groups" means groups comprising linear, branched or cyclic saturated carbon atoms and hydrogen atoms. The term "aryl groups" means aromatic groups.

At least one alkyl group in the compounds cited above can be replaced by an alkenyl group, i.e., a group comprising linear, branched or cyclic unsaturated carbon atoms and hydrogen, for example an allyl group.

Preferred tin precursors are organometallic compounds of the type $SnR_4$ (R=alkyl group) or polyalkyl halides such as $Me_3SnCl$, $Me_2SnCl_2$, $MeSnCl_3$, $Et_3SnCl$, $Et_2SnCl_2$, $EtSnCl_3$, $iPrSnCl_2$ and the hydroxides $Me_3SnOH$, $Me_2Sn(OH)_2$, $Et_3SnOH$, $Et_2Sn(OH)_2$, the oxide $[Bu_3Sn]_2O$, or the acetate $Bu_3SnOC(O)Me$. These polyalkyl halides comprise at least one carbon-Sn bond and at least one hydrosoluble function, which renders them soluble in aqueous solvents, facilitating processing when preparing the catalyst.

The group VIII metal compound can be introduced in the form of an inorganic or organic complex selected, for example, when the group VIII metal is platinum, from hexachloroplatinic acid, hexahydroxyplatinic acid, dihydroxytetramine platinum, platinum diaminonitrite, or from organometallic complexes such as platinum bis-acetylacetonate.

Preparation of the catalyst includes simultaneous or successive introduction in any order of the group VIII metal, tin, optional halogen or halogenated compound, optional alkali or alkaline-earth metal, optional metalloid, and optional other chemical element. When the elements are introduced successively, once the first element has been introduced, the skilled person will then be able to adapt the conditions for introducing the other elements so as to obtain a catalyst with the characteristics defined above.

The metals can be introduced during any of the catalyst manufacturing steps using prior art techniques. As an example, the tin can be added to an alumina sol (U.S. Pat. No. 3,929,683) or when the support is being formed, for example using extrusion forming (U.S. Pat. No. 3,917,808) or by the oil drop method (U.S. Pat. No. 3,558,508). In a preferred implementation of the process for preparing the catalyst, the support is preferably initially impregnated using a solution of an alkali or alkaline-earth metal, the mixture is filtered then the recovered product is dried and calcined. The solid obtained is impregnated with an aqueous solution saturated with $CO_2$, containing at least one tin precursor in the form of $SnCl_2$ or, preferably, in the form of organometallic compounds containing at least one carbon-tin bond such as polyalkyl halides, for example $Me_3SnCl$, $Me_2SnCl_2$, $MeSnCl_3$, $Et_3SnCl$, $Et_2SnCl_2$, $EtSnCl_3$, $iPrSnCl_2$ and the hydroxides $Me_3SnCl$, $Me_2Sn(OH)_2$, $Et_3SnOH$, $Et_2Sn(OH)_2$, the oxide $[Bu_3Sn]_2O$, or the acetate $Bu_3SnOC(O)Me$. After leaving the solid and impregnating solution in contact for several hours, the product is filtered then optionally undergoes a drying step at 120° C. and an optional calcining step between 300° C. and 600° C., preferably between 450° C. and 550° C. The solid obtained is preferably impregnated-with an organic solution of at least one compound of a group VIII metal, the volume of the solution being in excess with respect to the retention volume of the support. After several hours contact, the product obtained is dried and calcined in air between 300° C. and 600° C., preferably in a stream of air for several hours.

In a further, preferred, implementation of the process for preparing the catalyst, the catalytically active base metal such as platinum is deposited in a plurality of steps before depositing the tin, to selectively deposit the tin on particles with a controlled size, i.e., on particles with a size that is larger than that of the final catalyst. As an example, the support is impregnated with an organic solution containing at least one organometallic platinum compound such as platinum acetylacetonate ($Pt(acac)_2$), the volume of the solution preferably being in excess with respect to the retention volume of the support. After leaving the solid and impregnating solution in contact for several hours, the product is filtered then dried and calcined in air between 300° C. and 600° C., preferably between 400° C. and 500° C., advantageously flus with air for several hours. It is then reduced in a stream of hydrogen between 300° C. and 600° C., preferably between 350° C. and 500° C. The catalyst is then transferred to the impregnation reactor without ingress of air, to deposit platinum again following exactly the same procedure as that given above. This can be carried out a number of times. To deposit the tin, the solid obtained is transferred to a reactor without ingress of air where tin impregnation is carried out by bringing an aqueous or organic solution of an organometallic tin compounds into contact for several hours, the volume of the solution preferably being in excess with respect to the retention volume of the support. The reaction is advantageously carried out in a stream of hydrogen into the impregnating solution. The solid obtained is filtered, dried and reduced in a stream of hydrogen between 300° C. and 600° C. If the catalyst contains an alkali or alkaline-earth metal, it can be added at any stage during the preparation. Preferably, it is introduced once tin impregnation has been carried out. Finally, the catalyst is calcined.

To dehydrogenate short paraffins, regardless of the process by which it is prepared, the catalyst advantageously undergoes a final step consisting of an oxychlorination treatment, generally carried out in a stream of a gas comprising oxygen, chlorine and possibly water using any technique that is known to the skilled person (U.S. Pat. No. 3,875,049).

In contrast, when dehydrogenating long chain paraffins, it is not advisable to carry out an oxychlorination treatment on the catalyst, as the presence of chlorine reduces the performances in such processes. Further, it is preferable to use precursors of metals comprised in the catalyst which may not contain chlorine. As an example the platinum precursor may be platinum acetylacetonate, and the tin precursor may be $Me_3SnCl$ or $Me_3SnOH$.

Before use, and regardless of the type of compounds to be dehydrogenated, the catalyst is reduced in hydrogen, for example between 200° C. and 600° C., to obtain an active metallic phase. The procedure for this treatment consists, for example, in slowly raising the temperature in a stream of hydrogen to the maximum reduction temperature, for example in the range 200° C. to 600° C., preferably in the range 250° C. to 550° C., more preferably in the range 350° C. to 550° C., followed by a constant temperature stage for 1 to 6 hours at that temperature.

This reduction can be carried out immediately after calcining or subsequently on site. It is also possible to directly reduce the dried product on site.

Any other preparation method is suitable that results in a reduced catalyst with a strong interaction between at least a fraction of the tin and a group VIII metal and in the partially oxidised form containing at least 10% of the tin in the form of tin with an oxidation state of 0, where the reduced tin species $Sn^0$ has an isomer shift in the range 0.80 to 2.60 mm/s and a quadrupolar splitting in the range 0.65 to 2.00 mm/s.

When the catalyst of the process of the present invention contains sulphur, the sulphur is introduced into the formed, calcined catalyst containing the metal or metals cited above, either in situ prior to the catalytic reaction, or ex situ. Optional sulphurisation is carried out after reduction. With in situ sulphurisation, if the catalyst has not already been reduced, reduction takes place before sulphurisation. With ex situ sulphurisation, reduction is carried out followed by sulphurisation. Sulphurisation is carried out in the presence of hydrogen using any sulphurisation agent that is well known to the skilled person, such as dimethyl sulphide or hydrogen sulphide. As an example, the catalyst is treated with a feed containing dimethyl sulphide in the presence of hydrogen, with a concentration such that the sulphur/metal atomic ratio is 1.5. The catalyst is then kept at about 400° C. for about 3 hours in the stream of hydrogen before injecting the feed.

The different paraffin and naphthene dehydrogenation processes are distinguished by the choice of operating conditions and the composition of the feed. The operating conditions are adjusted depending on the feed to be treated, to obtain the best pressure-temperature yield and activity balance in a manner that is known to the skilled person.

The paraffin dehydrogenation reaction is generally carried out at a pressure in the range 0.02 to 2 MPa, preferably in the range 0.1 to 1 MPa, and at a temperature in the range 400° C. to 800° C. depending on the nature of the feed. The temperature is advantageously in the range 400° C. to 550° C. for a feed essentially comprising isopentane. The temperature is advantageously in the range 450° C. to 550° C. for a feed principally comprising paraffins containing 9 to 22 carbon atoms per molecule. The feed can also contain unsaturated hydrocarbons containing 3 to 22 carbon atoms per molecule. The mass flow rate of the feed treated per unit mass of catalyst is generally in the range 0.5 to 100 kg/kg/h. It may be advantageous to use hydrogen as the diluent. The hydrogen/hydrocarbon mole ratio is generally in the range 0 to 20, preferably in the range 0 to 6.

The naphthene dehydrogenation reaction is generally carried out at a pressure in the range 0.1 to 2 MPa, preferably in the range 0.1 to 1 MPa and at a temperature in the range 200° C. to 400° C. depending on the nature of the feed. The mass flow rate of the feed treated per unit mass of catalyst is generally in the range 0.5 to 100 kg/kg/h.

The following examples illustrate the invention without limiting its scope.

EXAMPLE 1

Not in Accordance with the Invention

A catalyst A was prepared comprising 0.35% of platinum, 0.55% of tin, 1% by weight of chlorine and 1% by weight of potassium deposited on a gamma alumina support with a specific surface area of 200 $m^2/g$.

500 $cm^3$ of an aqueous solution containing tin chloride was added to 100 g of alumina support in the presence of hydrochloric acid and nitric acid. It was left in contact for 3 hours, filtered, dried at 120° C. then calcined for 2 hours at 500° C. in an air flow of 100 liters per hour. The solid was then brought into contact with 500 cm³ of an aqueous solution of hexachloroplatinic acid and hydrochloric acid. It was left in contact for 3 hours then drained. It was dried for 1 hour at 120° C. then calcined for 2 hours at 500° C. in an air flow of 100 liters per hour. 100 cm³ of an aqueous potassium carbonate solution was then added and it was dried for 1 hour at 120° C. followed by calcining for 2 hours at 500° C. in an air flow of 100 liters per hour.

Catalyst A was then reduced at 500° C. for 4 hours in a hydrogen flow of 100 liters per hour. Scanning electron microscope (SEM) analysis showed a very good dispersion of the metallic phase with particle sizes of less than 1.2 nm.

EXAMPLE 2

In Accordance with the Invention

A catalyst B was prepared with the same formulation as catalyst A.

Catalyst B was prepared by depositing platinum in two steps prior to depositing the tin. 100 g of alumina support was brought into contact with 500 cm³ of an organic solution of platinum bis-acetylacetonate. It was left in contact for 12 hours then drained. It was dried for 1 hour at 120° C. then calcined for 2 hours at 350° C. in an air flow of 100 liters per hour. The catalyst was then reduced at 450° C. for 4 hours in a hydrogen flow rate of 100 liters per hour. After this reduction step, the solid was transferred without ingress of air into a reactor containing 500 cm³ of an organic platinum bis acetylacetonate solution. It was left in contact for 12 hours then drained. It was dried for 1 hour at 120° C. then calcined for 2 hours at 350° C. in an air flow of 100 liters per hour. The catalyst was then reduced at 450° C. for 4 hours in a flow of hydrogen of 100 liters per hour. The solid obtained was transferred, without ingress of air, into a reactor containing 500 cm³ of an organic solution containing the necessary quantity of tetrabutyltin to deposit 0.55% by weight of tin on the catalyst, bubbling through hydrogen at 20° C. After 24 hours of contact, the reaction mixture was filtered, washed then dried at 70° C. The catalyst was then reduced for 4 hours at 450° C. in 100 liters per hour of hydrogen. 100 cm³ of an aqueous potassium carbonate solution was then added and it was dried for 1 hour at 120° C. followed by calcining for 2 hours at 500° C. in an air flow of 100 liters per hour. The catalyst then underwent an oxychlorination treatment at 500° C. for 4 hours in an air flow of 100 liters per hour containing the quantity of chlorine necessary to deposit 1% by weight of chlorine and a quantity of water corresponding to a H₂O/Cl mole ratio of 20.

Catalyst B was then reduced at 500° C. for 4 hours in a hydrogen flow of 100 liters per hour. Scanning electron microscope (SEM) analysis showed a very good dispersion of the metallic phase with particle sizes of less than 1.2 nm.

EXAMPLE 3

For $^{119}$Sn Mössbuaer spectroscopic characterization, reduced catalysts A and B obtained as described above were treated using a χsorb apparatus to carry out dynamic oxygen chemisorption measurements in combination with on-line chromatographic analysis to furnish the oxygen consumption. The volume of the cell used was about 10 cm³.

In each case, 2 grams of catalyst were activated at 500° C. for 4 hours in a flow of hydrogen. After cooling to ambient temperature, and flushing with helium, the number of pulses of oxygen necessary to saturate the catalyst was applied to the catalyst, i.e., until constant surface area peaks were obtained that corresponded to the total oxygen consumption. The volume of a pulse of pure oxygen was 0.22 cm³. Pulse injection was continued until at least 10 peaks were obtained with a constant surface area, corresponding to the oxygen that had not reacted with the catalyst. Then after flushing in helium at ambient temperature, the treatment cell was directly sealed without ingress of air. The Mössbuaer spectroscopic analyses were carried out with this cell, which was then cooled to the temperature of liquid nitrogen using the flow cryostat. The spectrum was then recorded in transmission mode using the apparatus described above. The data acquisition time was selected to produce the best signal/noise ratio. In the present examples, it was 48 hours.

The results, comprising identification, characteristics and amounts of different tin species present for catalysts A and B reduced then partially re-oxidised in a controlled manner by oxygen pulses are shown in Table 1.

TABLE 1

| Catalyst | Species attribution | IS (mm/s) | QS (mm/s) | LW (mm/s) | Proportion (%) |
|---|---|---|---|---|---|
| A | $Sn^{IV}$ | −0.03 (0.01) | 0.55 (0.01) | 0.82 (0.02) | 63.4 |
|   | $Sn^{II}$ | 3.33 (0.02) | 2.11 (0.08) | 0.82 (0.04) | 28.5 |
|   | $Sn^{0}$ | 1.55 (0.08) | 1.12 (0.01) | 1.07 (0.09) | 8.1 |
| B | $Sn^{IV}$ | 0.03 (0.01) | 0.48 (0.01) | 0.86 (0.01) | 59.9 |
|   | $Sn^{II}$ | 3.17 (0.02) | 1.15 (0.08) | 0.86 (0.01) | 4.2 |
|   | $Sn^{0}$ | 1.29 (0.02) | 1.19 (0.03) | 1.08 (0.04) | 35.9 |

IS: isomer shift δ with respect to BaSnO₃
QS: quadrupolar splitting Δ
LW: mid-height peak width The values given in brackets are the standard deviations.

As can be seen, for the same formulation, catalyst B of the invention contains an amount of species $Sn^0$ contained in the phase $Pt_xSn_y$ (QS of 1.19 mm/s) that is much higher than that determined for catalyst A that is not in accordance with the invention and which corresponds to prior art catalysts.

EXAMPLE 4

Catalysts A and B, in the reduced state, and as described above were tested in an isobutane dehydrogenation test carried out in an isothermal quartz tube reactor. 1 g of catalyst was reduced at 550° C. for 2 hours in a stream of hydrogen of 2 liters per hour. After injecting the feed, the temperature was stabilised at 550° C. The different gaseous effluents were analysed on-line by gas chromatography. The operating conditions were as follows:

| Feed | iC4 Liquid Air N35 |
|---|---|
| Temperature | 550° C. |
| Total pressure | 0.1 MPa |
| Feed flow rate | 200 g per g of catalyst |
| Hydrogen/feed | 1 (molar) |

The performances obtained are shown in Table 2:

TABLE 2

| Catalyst | Duration (hours) | Isobutane conversion (wt %) | Isobutene selectivity (wt %) | Isobutene yield (wt %) |
|---|---|---|---|---|
| A | 1 | 25.2 | 95.5 | 24.1 |
|   | 4 | 19.5 | 96.1 | 18.7 |

TABLE 2-continued

| Catalyst | Duration (hours) | Isobutane conversion (wt %) | Isobutene selectivity (wt %) | Isobutene yield (wt %) |
|---|---|---|---|---|
| | 8 | 13.8 | 96.3 | 13.3 |
| B | 1 | 25.8 | 95.6 | 24.7 |
| | 4 | 23.9 | 96.0 | 22.9 |
| | 8 | 16.9 | 96.1 | 16.2 |

The isobutene yields produced by catalyst B for different reaction periods were substantially higher than those for catalyst A. The high isobutane conversion with catalyst B is evidence of the better activity and better stability of catalyst B compared with catalyst A.

What is claimed is:

1. A process for dehydrogenating organic compounds, comprising bringing a hydrocarbon feed into contact with a catalyst in the reduced state, comprising at least one support, at least one group VIII metal, and at least tin, at least a portion of which is in the form of a reduced species with oxidation state 0 when said catalyst is in the partially oxidised state, said species having an isomer shift IS in the range 0.80 to 2.60 mm/s and a quadrupolar splitting in the range 0.65 to 2.00 mm/s, wherein when said catalyst is in the partially oxidised state, said reduced tin species with oxidation state 0 represents at least 10% of the tin present in the catalytic mass.

2. A process according to claim 1, wherein when said catalyst is in the partially oxidised state, said reduced tin species with oxidation state 0 represents at least 12% of the tin present.

3. A process according to claim 1, wherein in the partially oxidised state, said reduced tin species with oxidation state 0 represents at least 15% of the tin present.

4. A process according to claim 1, wherein in the partially oxidised state, said reduced tin species with oxidation state 0 represents at least 20% of the tin present.

5. A process according to claim 1, wherein in the partially oxidised state, said reduced tin species with oxidation state 0 represents at least 25% of the tin present.

6. A process according to claim 1, wherein in the partially oxidised state, said reduced tin species with oxidation state 0 represents at least 30% of the tin present.

7. A process according to claim 1, wherein said reduced tin species with oxidation state 0 has an isomer shift in the range 0.80 to 1.50 mm/s.

8. A process according to claim 1, wherein said reduced tin species with oxidation state 0 has a quadrupolar splitting in the range 0.80 to 2.00 mm/s.

9. A process according to claim 1, wherein said reduced tin species with oxidation state 0 has a quadrupolar splitting in the range 0.90 to 1.90 mm/s.

10. A process according to claim 1, wherein said reduced tin species with oxidation state 0 has a quadrupolar splitting in the range 0.95 to 1.50 mm/s.

11. A process according to claim 1, wherein in the partially oxidised state, the catalyst contains $Sn^{2+}$ species.

12. A process according to claim 1, wherein the catalyst comprises at least one alkali metal or alkaline-earth metal.

13. A process according to claim 1, said catalyst further comprising at least one halogen or halogenated compound.

14. A process according to claim 1, said catalyst further comprising at least one metalloid.

15. A process according to claim 1, wherein the group VIII metal of the catalyst is platinum.

16. A process according to claim 1, wherein the catalyst support is alumina.

17. A process according to claim 1, wherein the catalyst contains metallic particles less than 2 nm in size.

18. A process according to claim 1, wherein the organic compounds are short chain paraffins containing 2 to 5 carbon atoms.

19. A process according to claim 18, wherein the hydrocarbon feed to be treated is brought into contact with the catalyst at a pressure in the range 0.02 to 2 MPa, at a temperature in the range 400° C. to 800° C. and at a mass flow rate of treated feed per unit mass of catalyst in the range 0.5 to 100 kg/kg/hour.

20. A process according to claim 1, wherein the organic compounds are long chain paraffins containing 6 to 22 carbon atoms.

21. A process according to claim 1, wherein the organic compounds are naphthenes.

22. A process according to claim 21, wherein the naphthenes comprise at least one member selected from the group consisting of methylcyclohexane and cyclohexane.

23. A process according to claim 21, wherein the hydrocarbon feed to be treated is brought into contact with the catalyst at a pressure in the range 0.1 to 2 MPa, at a temperature in the range 200° C. to 400° C. and at a mass flow rate of treated feed per unit mass of catalyst in the range 0.5 to 100 kg/kg/hour.

24. A process according to claim 1, wherein the catalyst further comprises indium.

25. A process according to claim 1, wherein the catalyst in the partially oxidized state means a catalyst oxidized in pulses with a gas comprising oxygen.

26. A process according to claim 25, wherein the gas is oxygen.

27. A process according to claim 1, wherein the IS is 1.10–1.40 mm/s.

28. A process according to claim 1, wherein IS is 1.10–1.40 mm/s and QS is 0.95–1.50 mm/s.

29. A process according to claim 1, wherein when catalyst is in the partially oxidised state, the catalyst comprises about 35.9% of $Sn^0$ with respect to the tin present in the catalytic mass.

* * * * *

UNITED STATES PATENT AND TRADEMARK OFFICE
CERTIFICATE OF CORRECTION

PATENT NO. : 6,600,082 B2
DATED : July 29, 2003
INVENTOR(S) : Fabienne Le Peltier et al.

It is certified that error appears in the above-identified patent and that said Letters Patent is hereby corrected as shown below:

<u>Title page,</u>
Item [73], Assignee, reads "Rueii-Malmaison" should read -- Rueil-Malmaison Cedex --

Signed and Sealed this

First Day of June, 2004

JON W. DUDAS
*Acting Director of the United States Patent and Trademark Office*